United States Patent [19]

Ruschak et al.

[11] Patent Number: 5,110,553
[45] Date of Patent: May 5, 1992

[54] AUTOMATIC SAMPLE PREPARATION FOR ANALYSIS OF SAMPLE PARTICLES

[75] Inventors: Michael L. Ruschak, Sewickley Township, Allegheny County; William D. McAninch, Allegheny Township, Allegheny County; Dan A. Anderson, Greensburg, all of Pa.

[73] Assignee: Aluminum Company of America, Pittsburgh, Pa.

[21] Appl. No.: 279,014

[22] Filed: Dec. 2, 1988

[51] Int. Cl.$^5$ .................... G01N 1/10; G01N 21/62
[52] U.S. Cl. .................... 422/68.1; 73/863.51; 73/DIG. 9; 422/72; 422/102; 422/62; 422/82.05; 436/73; 436/174
[58] Field of Search .................... 422/50, 52, 62, 68.1, 422/72, 82.05, 82.09, 102, 103; 73/863.51, 863.91, 864.22, DIG. 9; 356/36; 436/73, 171, 174, 181

[56] References Cited

U.S. PATENT DOCUMENTS

| | | | |
|---|---|---|---|
| 3,607,099 | 9/1971 | Beer | 73/864.22 |
| 3,659,944 | 5/1972 | Bojic | 73/DIG. 9 |
| 3,756,082 | 9/1973 | Bardenheuer et al. | 73/DIG. 9 |
| 3,881,355 | 5/1975 | Nelson et al. | 73/DIG. 9 |
| 3,963,420 | 6/1976 | Matsumoto et al. | 436/73 |
| 3,985,031 | 10/1976 | Franz | 73/DIG. 9 |
| 4,598,596 | 7/1986 | Wiseman et al. | 73/864.22 |
| 4,743,155 | 5/1988 | Carey et al. | 73/863.51 |
| 4,783,417 | 11/1988 | Genna | 436/174 |
| 4,799,393 | 1/1989 | Uffenheimer | 73/864.22 |
| 4,823,622 | 4/1989 | Nohl et al. | 73/864.22 |
| 4,936,371 | 6/1990 | McAninel et al. | 164/4.1 |
| 5,030,577 | 7/1991 | Genna et al. | 436/56 |

FOREIGN PATENT DOCUMENTS

0049243 3/1985 Japan .................... 73/863.41

OTHER PUBLICATIONS

Rammler, Roland W., "Low-Investment Carbonization Process for Coals Makes Liquid, Gas and Boiler Fuel", Oil and Gas Journal, Nov. 9, 1981, pp. 291-306.
Colijn, Hendrik, "Weighing and Proportioning of Bulk Solids", Series on Bulk Materials Handling, vol. 1(1975), No. 1, p. 262.
Zenz, Frederick A. et al., "Fluidization and Fluid-Particle Systems", p. 54, and pp. 398-407.
Ionics, Incorporated, "Instruction Manual, Digichem 3000 and 4000 Series, Programmable Chemical Analyzers", pp. 4-20-4-21 and 8-10-8-11.

Primary Examiner—Peter Kratz
Attorney, Agent, or Firm—Elroy Strickland

[57] ABSTRACT

Apparatus for analyzing the compositions of metal particles. The apparatus includes a cup which, when filled to maximum capacity will hold substantially the same amount of metal particles each time it is filled, and has a profile that diverts any excess particles away from the cup. A vessel is provided for receiving the particles from the cup and for dissolving the particles when a solvent is sent to the vessel. A known amount of solvent is directed to the vessel to dissolve the particles and thereby provide a dissolved sample of metal for analysis. An optical emissions spectrometer receives the dissolved sample and is employed to produce emission spectra from the dissolved sample. The spectra is compared to emission spectra produced by a known amount of a known alloy of the same metal as the sample metal to determine the composition of the sample metal.

10 Claims, 2 Drawing Sheets

AUTOMATIC SAMPLE PREPARATION FOR ANALYSIS OF SAMPLE PARTICLES

BACKGROUND OF THE INVENTION

The present invention relates generally to analysis of solid metal particles and particularly to a method and apparatus that provides a repeatably consistent amount of sample metal and solvent for the analytical process.

Patent application Ser. No. 826,988, and now U.S. Pat. No. 4,783,417 filed Feb. 7, 1986, discloses a method and apparatus for making metal flakes from a pool of molten metal and transporting the same to apparatus for dissolving the flakes and for analyzing the dissolved metal of the flakes for alloy composition of the base metal of the flakes.

In the development that lead to the filing of the above application, a "known" amount of sample material for analysis was supplied to a reaction vessel having a chamber for dissolving the sample material. The known amount of the sample was provided by a process that weighed the sample and delivered it to the dissolution chamber. The weighing process, however, was somewhat time consuming, taking on the order of sixty to ninety seconds, and unreliable because an accurate sample size could not be weighed within the time constraints necessary to obtain the results of analysis as quickly as possible. An inaccurate sample size caused the results of the analysis of the sample to be inaccurate i.e., the more accurate the size of the metal sample the more accurate is the result of the analysis of the composition of the sample.

After the sample was weighed and delivered to the reaction vessel, a measured amount of solvent was supplied to the dissolution chamber of the vessel for dissolving the metal flakes. For example, with a sample of aluminum flakes weighing approximately 0.1 gram, 10 milliliters 50% HCL were used to dissolve the aluminum sample. The HCL was measured in a glass tube provided with an optical sensor. When a suitable amount of HCL was supplied to the tube, the sensor operated to stop the supply and transfer the contents of the tube to the reaction vessel. The apparatus and components necessary to operate the process were unduly mechanically complex such that the process was not reliable.

SUMMARY OF THE INVENTION

It is therefore an objective of the invention to provide a reliable process for measuring and transferring a solvent to a reaction vessel.

Another objective of the invention is to provide an amount of sample particles that is substantially more accurate and in a more rapid manner than that provided by the above weighing system.

A further objective of the invention to provide repeated analyses of metal particles without degradation of precision and accuracy of the results of the analyses over time.

Yet another objective of the invention is to greatly reduce, if not eliminate altogether, analytical errors due to sample alliquoting procedures.

The above objectives are accomplished by, inter alia, a cup configured to provide a known amount of metal particles each time it is filled to capacity, and having an upper edge configured to divert excess particles away from the cup. When the cup is filled, it is emptied into a dissolution vessel to provide a dissolved sample of the metal particles. The configuration of the cup ensures that the vessel receives an accurate amount of sample particles for analysis, which amount is repeatedly provided each time the analysis of a sample is made. In repeated tests of a cup of the invention, the weight of the samples averaged 0.088 grams ±0.009 grams. The time required to fill the cup and direct its contents to the dissolution vessel averaged five seconds.

The particle sample provided by the cup is dissolved in the dissolution vessel by a precise, known amount of solvent. Such an amount is provided by a pipette system described in detail below. The time to fill a ten milliliter pipe of the system with solvent and supply the same to the dissolution vessel takes 5 seconds.

Analysis is effected preferably by an optical emission spectrometer. A dissolved sample of metal is directed to the optical emission spectrometer, and an emission spectra is produced from the dissolved sample. The emission spectra is compared to emission spectra produced by a known amount of a known alloy of the same base metal as the sample metal to determine the composition of the sample metal.

Repeatably accurate emission spectra are produced from each dissolved sample because of the repeatedly accurate amounts of sample metal supplied for analyses and the repeatably accurate amounts of solvent supplied to dissolve each sample.

THE DRAWINGS

The objectives and advantages of the invention will be better understood from consideration of the following detailed description and the accompanying drawings in which.

PREFERRED EMBODIMENT

Figure 1:
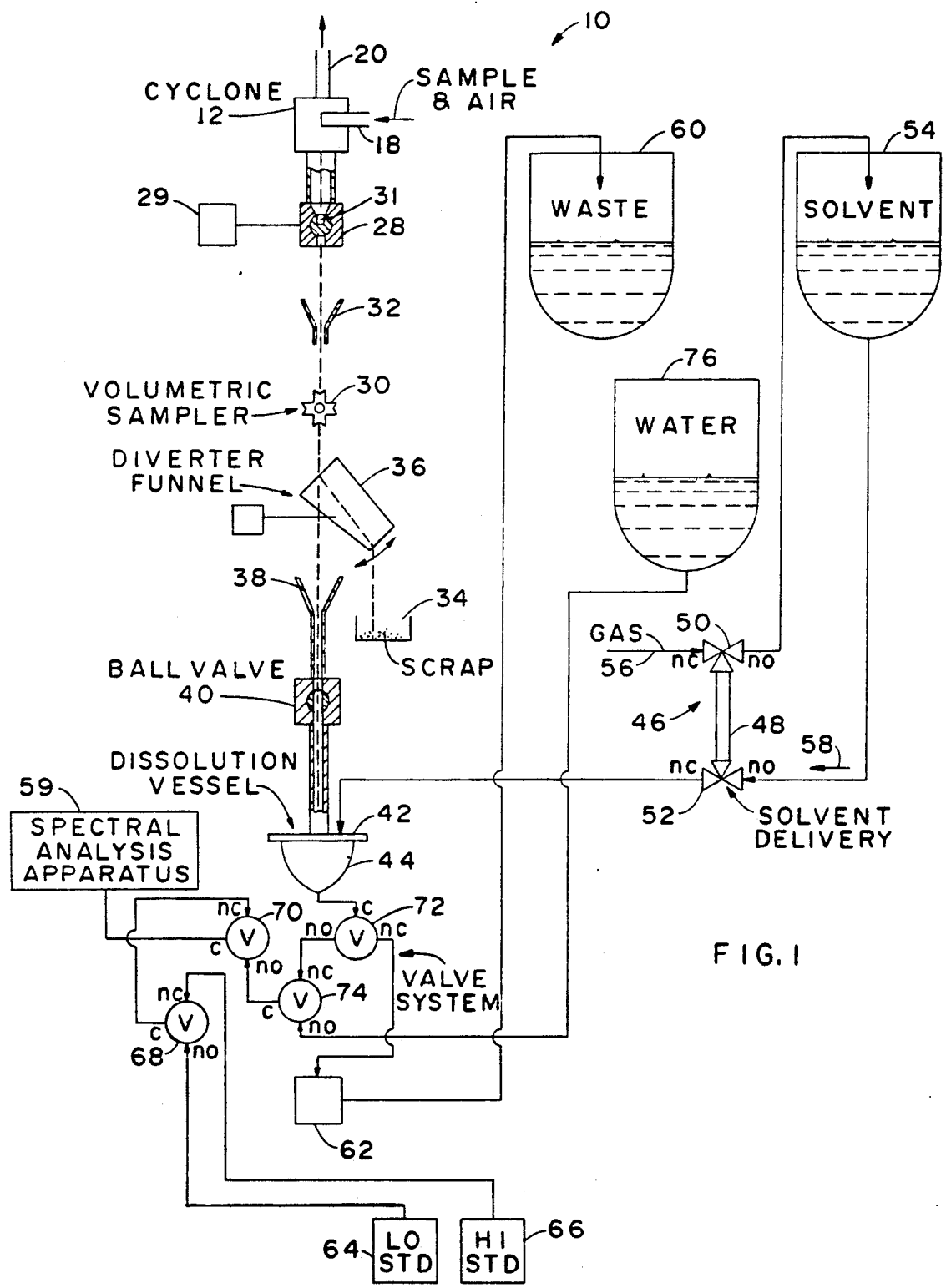
FIG. 1 is a schematic representation of the particle sampling and dissolving apparatus of the invention.
Figure 2:
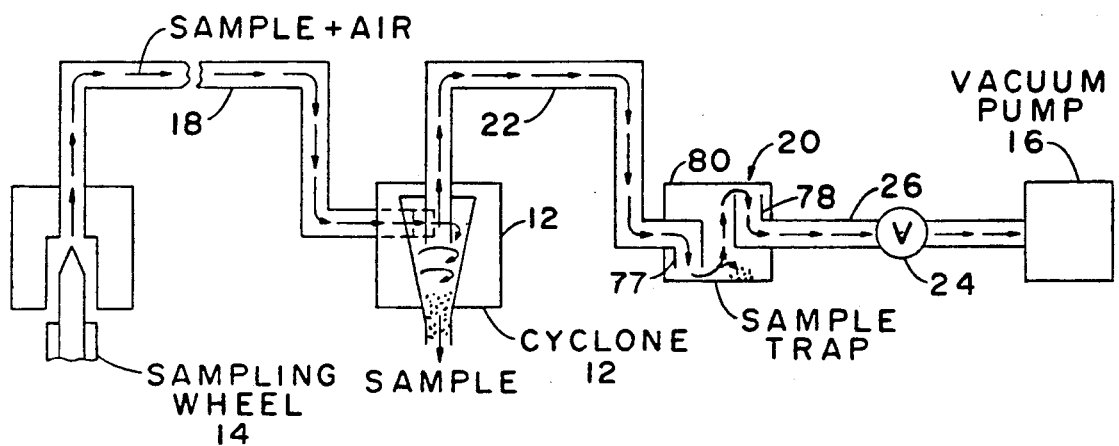
FIG. 2 is a schematic representation of a vacuum system for conveying the particles of FIG. 1.

Referring now to FIG. 1 of the drawings, an apparatus 10 is shown schematically for providing accurate preparation of the metal particles of a base metal for subsequent analysis. More particularly, the particles are collected in a cyclone device 12 after being conveyed thereto from a source of particles. In FIG. 2 of the drawings the source is a sampling wheel 14. The wheel has peripheral serrations (not shown), which are rotated in a pool of molten metal (not shown). Molten metal droplets collect on the serrations when they rotate out of the molten pool. The molten metal freezes on the serrations to form solid particles. The particles are transported in FIG. 2 from the wheel to cyclone 12 by being entrained in a gas stream provided by a vacuum pump 16. The gas stream is created when the vacuum provided by the pump draws air into the end of a conduit 18 located adjacent wheel 14. From the cyclone, the gas travels to a particle trap 20 via a conduit 22.

The particles collected and measured for analysis in the present invention can, of course, be supplied by sources other than a sampling wheel.

The particles entrained in the gas stream and carried to cyclone 12 circulate in the cyclone with little or no particles traveling to trap 20, i.e., cyclone 12 is sized and designed for a particular particle size (or narrow range of sizes) such that the particles are collected and retained in the cyclone even though the gas stream itself passes through the cyclone and travels to pump 16.

The particles collected in cyclone 12 are separated from the gas stream by interrupting the flow of the stream. This can be accomplished by closing a valve 24 located in a conduit 26 extending between the vacuum pump and the particle trap. When the valve is closed, the pump draws from another source of atmosphere until the valve is reopened.

Cyclone 12 is vertically oriented such that when the gas stream is interrupted, the particles contained in the cyclone fall by gravity from the cyclone to a receptacle 28 located beneath the cyclone. The receptacle is then rotated by an actuator 29 to dump the particles to a sample cup 30 via a funnel 32. The movement of particles in FIG. 1 is shown by a straight dash line descending from the cyclone.

A receptacle that has been found particularly suitable for receiving the contents from cyclone 12 and for transferring the same to cup 30 is a ball valve that is modified to provide a recess 31 in the solid ball of the valve in place of the usual passageway that extends through the ball. The ball is connected to actuator 29 so that it can be rotated for the filling and emptying process. Preferably, the cyclone is mounted on and attached to the upper surface of the valve structure so that the valve seals the cyclone while the gas stream flows through the cyclone and the particles collected in the cyclone fall directly into the recess of the ball.

Figure 3:
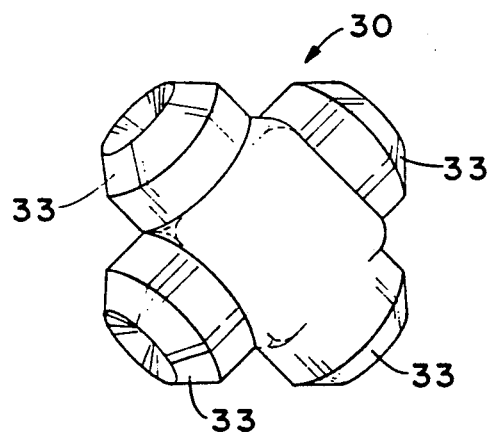
FIG. 3 is an isometric view of a compound cup arrangement that is part of the apparatus of FIG. 1.

Cup 30 is volumetrically sized such that each time it is filled to capacity the cup provides a known, exact amount of sample metal for the analysis process. The shape of the cup is such that it does not retain particles on its outside surface, the outside surface being smooth, and the upper edge of the cup having a bevelled surface 33 (FIG. 3). The bevelled surface and smooth sides of the cup divert excess particles from the cup such that when the cup is emptied for the analysis process only its contents will be received for analysis. As shown in FIG. 1, excess particles are diverted from the cup to a scrap location 34 by a diverter funnel 36. When the cup is filled and excess particles diverted, the funnel is moved to a position over a third funnel 38.

Cup 30 can be a single container located to receive sample particles from cyclone 12. Such a cup can be emptied by a suitable mechanism (not shown) that rotates the cup from an upright position to a position that transfers its contents to funnel 36 by gravity. Preferably, however, the cup is part of an integral cup structure, such as shown in FIG. 3, that includes two or more cups so that when one cup is filled and rotated to empty its contents, another cup is rotated into place to receive a next supply of particles from cyclone 12. FIG. 3 of the drawings shows four such cups in the form of symmetrical cross so that a 90° rotation of a filled cup places an empty cup into position to be filled.

Beneath third funnel 38 is located a ball valve 40, and beneath 40 is the lid 42 of a reaction vessel 44 (where the sample received in cup 30 is sent to be dissolved). Preferably, funnel 38, ball valve 40 and lid 42 are connected together so that the particles leaving funnel 36 will fall in a straight line to the reaction vessel 44 without disturbance. Similarly, the ball valve is preferably an integral part of lid 42 so that the valve can operate to open vessel 44 to pass the sample from funnel 38 into the vessel, and then close the vessel after the sample is received by the vessel. In this manner, the vessel is sealed when dissolution of the sample takes place, thereby preventing the escape of any fumes from the vessel during the dissolving process.

To ensure repeatably accurate results of the analysis of each sample received in vessel 44 from cup 30, the vessel must receive the same amount of solvent for dissolving the solid particles of each sample. This is accomplished by a pipette system 46. The system includes a single, vertically disposed pipe or tube 48, the ends of which are respectively fitted with three-way, solenoid operated valves 50 and 52. The upper valve 50 has one inlet connected to the top of a vessel containing a solvent 54, while a second inlet is connected to a supply 56 of a low pressure gas. The third port of the three-way valve of 50 is connected to the upper end of pipe 48.

The lower valve 52 has one inlet connected to receive solvent under force of gravity from supply 54, and one outlet connected to reaction vessel 44. The third port of valve 52 is connected to the lower end of pipe 48.

Pipe 48 is filled to capacity by opening the inlets of valves 50 and 52 connected to supply 54. As indicated by the letters "no" in FIG. 1, these ports (inlets) of each valve are normally open, while the ports connected to gas supply 56 and vessel 44 are normally closed ("nc"). The ports of the valves connected to the ends of the tube are common ("c").

Pipe 48 is filled from the bottom, as indicated by arrow 58. The normally open port of the upper valve ensures that air is not trapped in the tube, and that the tube thus fills with solvent; any excess solvent returns to supply 54.

When tube 48 is filled, the solenoids (not shown) that operate valves 50 and 52 are simultaneously activated to close the normally open ("no") inlets of the valves, and open the ports connected to gas supply 56 and to reaction vessel 44. The supply of gas enters the tube and is under sufficient pressure to drive the contents of the tube immediately from tube, through lower valve 52, to vessel 44.

The content of the tube when filled is transferred to the reaction vessel each time the vessel receives the contents of cup 30. In this manner, the amount of sample metal provided to vessel 44 relative to the amount of solvent is always the same. Dissolution of the sample is ordinarily completed under a minute, the exact time of dissolution dependent upon the size of the sample particles and the strength of the solvent, among other factors.

The transfer of the solvent to vessel 44 when the particles reach the vessel is preferably effected by a microprocessor (not shown) programmed to control the operations of the apparatus, as thus far described.

When dissolution of the sample is completed, at least a portion of the dissolved, liquid sample is pumped from vessel 44 to spectral analysis apparatus 59. A pump (not shown) in apparatus 59 can be used for this purpose. The apparatus is preferably a commercially available inductively coupled excited plasma-optical emission spectrometer. In such apparatus, a liquid sample is passed into an inductively coupled argon plasma. Alloying elements in the plasma emit electromagnetic radiation, which radiation is optically examined by the spectrometer of the apparatus. The apparatus provides an analysis of the sample metal.

Any dissolved sample not sent to apparatus 59 is pumped to a waste container 60 by a pump 62.

The apparatus of 59 performs the analysis by comparing the spectra emitted by the sample metal to spectra emitted by a known amount of a known alloy of the same base metal as the sample metal. In FIG. 1, the "known" alloy is provided by two aqueous standards 64 and 66. The first, "low" standard (64) is the same base metal as that of the sample but contains a minimum percent of impurities by way of alloying elements. The other standard (66) is the same base metal as the sample and "low" standard but contains a substantially greater amount of alloy elements.

The analysis is accomplished in the following manner. The apparatus of 59 is preferably calibrated automatically upon start-up of the system, as thus far described, then at programmable intervals throughout the length of a run during which multiple samples are provided for analysis, i.e., each liquid standard is pumped by the pump in apparatus 59 to the plasma exitation portion of 59, and the emission intensity of each element in each standard is measured. The measured intensities of the elements in the high and low standards provide high and low data points for calculating a curve between the points for each element. To determine the concentrations of the elements in the sample, the intensitives are measured and the concentrations are read off the curves.

The above-mentioned microprocessor can be employed to manipulate the data obtained in the calibration process, from which the curves are provided. The microprocessor also controls the various components of the system, as mentioned above, in carrying out the sequence of operation of the apparatus of the invention. Such a microprocessor thus instructs apparatus 59 when to "calibrate" and thereby provides the curves, and then makes the comparisons to determine element concentrations when analyzing the sample provided by cup 30.

The control of apparatus 59 by the microprocessor includes control of four three-way valves 68, 70, 72 and 74. The calibration standards of 64 and 66 are pumped by the pump in apparatus 59 through valves 68 and 70. When the low standard is called for by the microprocessor, the standard is pumped through a normally open "no" inlet of valve 68, through a common ("c") outlet of 68 to a normally closed ("nc") inlet of valve 70. This latter inlet, however, is ordered opened by the microprocessor, and a normally open inlet of 70 closed, by the microprocessor, so that the low standard liquid can pass through 70 to apparatus 59.

When the high standard of 66 is called for, the normally closed inlet of valve 68 is opened, so that the flow from 66 enters the valve, and the normally open inlet of 68 closed. From 68, the standard travels through the common outlet (c) of 68 to the normally closed inlet of 70, which is now ordered open, and the normally open inlet of 70 ordered closed. This directs the standard to apparatus 59 through the common outlet "c" of valve 70.

When the dissolved sample is ready for analysis, valve 72 has already received the sample through a "common" inlet "c" of the valve. The sample travels through a normally open outlet of 72 to a normally closed inlet of valve 74. This inlet is now ordered open, and a normally open inlet of 74 closed so that the sample passes through the common port "c" of 74 to the lower, normally open inlet of valve 70. From 70, the sample flows to apparatus 59, the upper inlet of 70 being closed.

The system is also shown provided with a supply of water 76 in FIG. 1 for flushing spectral analysis apparatus 59 and certain components that conduct liquids to the apparatus. In this manner, each time the spectral analysis apparatus is used, it will not be contaminated with residual contents of a prior sample and standard materials. As shown in FIG. 1, water flushing is provided whenever the spectrometer is free of sample or standard liquids. This is accomplished by directing the water to a normally open inlet of valve 74, and through the common outlet of 74 to the normally open inlet of valve 70. From 70, the water flows through common outlet "c" of 70 to apparatus 59.

When the liquid standard from 64 is directed to apparatus 59 through valve 68, the normally closed port of valve 70 is opened and the normally open port is closed. When the liquid from standard 66 is directed to 59, the normally closed ports of valves 68 and 70 are opened and the normally open port of 70 closed. When the liquid from vessel 44 is directed to apparatus 59 through valve 72, the normally closed port of valve 74 is opened and the normally open valve is closed so that the liquid travels through 74 and to and through the normally open port of valve 70.

As discussed earlier, the cyclone device (12) employed to capture the particles entrained in the gas stream in conduit 18 (FIG. 2) is designed to capture the entrained particles. To ensure that no particles reach pump 16 (FIG. 2), a particle trap 20 is shown located between the cyclone and pump, the trap joining conduits 22 and 26 in FIG. 2. A trap structure that has proven effective is one in which two, substantially 90° elbow tubes 77 and 78 are provided in a container 80. The container is sealed to the ends of conduits 22 and 26 located at the opposite ends of container 80. The elbows extend from the ends of the conduits into the confines of the container, and terminate in the container in opposite directions, i.e., the inner end of elbow 77 faces in a downward direction, while the inner end of 78 faces upwardly. In this manner, any particle that may reach container 80 travels downwardly through elbow 77 and falls to the container wall from the elbow under force of gravity. The force of the gas stream drawn through the container by pump 16 is insufficient to overcome the force of gravity on the particle. The particle thereby remains in container 80.

While the invention has been described in terms of preferred embodiments, the claims appended hereto are intended to encompass all embodiments which fall within the spirit of the invention.

What is claimed is:

1. Apparatus for analyzing the composition of metal particles produced by means for making the particles, comprising:

means for forming a gas stream to transport the metal particles from the means for making the particles to a cyclone device for separating the particles from said stream before they are supplied to a cup, a cup located to receive metal particles from the means for producing said particles, which cup when filled to maximum capacity will hold substantially the same amount of metal particles from said means each time it is filled, said cup having an upper bevelled edge that is effective to divert particles not collected in the cup from the cup, means for directing excess particles from the cup to a scrap location, a dissolution vessel located to receive said amount of particles, said dissolution vessel provided with a ball valve that opens the vessel to receive the particles from the cup, and to close the vessel after the particles are received, means for receiving said amount of particles from the cup before said amount is received in the dissolution vessel, and for directing said amount to the dissolution vessel, means connected in fluid communication with the dissolution vessel for supplying a known amount of solvent to said vessel to dissolve said amount of metal particles received in the dissolution vessel and provide a dissolved sample of metal for analysis, and an optical emission spectrometer connected to receive the dissolved sample from the dissolution vessel for producing emission spectra from the dissolved sample, and for comparing said emission spectra with emission spectra produced by a known amount of a known alloy of the same metal as the sample metal to determine the composition of the sample metal.

2. Apparatus of claim 1 in which the means for creating the gas stream is a vacuum pump.

3. Apparatus of claim 1 including a ball valve disposed beneath the cyclone device, the ball of said valve having a recess for receiving the particles transported to the cyclone device.

4. Apparatus of claim 2 including particle trap means located between the cyclone device and the vacuum pump.

5. Apparatus of claim 1 in which the known amount of solvent is provided by a pipette arrangement comprised of a tube of a predetermined volume and a valve located at each end of the tube, said tube providing the known amount of solvent when the tube is filled with solvent.

6. Apparatus of claim 1 including means for producing standards for calibrating the optical emission spectrometer, and means for flushing the spectrometer, said flushing means including a valve system that provides flushing whenever the spectrometer is free of sample or standard materials.

7. Apparatus of claim 1 in which means for producing standards are included for calibrating the emission spectrometer, said standards being comprised of metal particles of two known but different alloys of the same metal as the dissolved sample, and dissolved in the same solvent and same ratio of solvent to sample as that used for dissolving the sample metal.

8. Apparatus for analyzing the composition of metal particles produced by means for making metal particles, comprising:

means for forming a gas stream to transport said particles from the means for making the particles through a conduit to a cyclone device, a cyclone device connected to said conduit for receiving the particles transported by the gas stream, means for interrupting the gas stream, receptacle means located beneath the cyclone device for receiving the particles from the cyclone device when the gas stream is interrupted, a cup provided with an upper bevelled edge for diverting particles not collected in the cup from the cup, said cup located beneath the receptacle means for receiving the particles from said receptacle means, and which when filled to maximum capacity will hold substantially the same amount of metal particles each time it is filled, means for directing excess particles from the cup to a scrap location, a dissolution vessel located to receive said amount of particles from the cup, means for receiving said amount of particles from the cup before said amount is received in the dissolution vessel, and for depositing said amount in the dissolution vessel, means connected to the dissolution vessel for supplying a known amount of solvent to the dissolution vessel to dissolve said amount of metal particles and provide a dissolved sample of metal for analysis, and an optical emission spectrometer connected to the dissolution vessel for receiving the dissolved sample for producing emission spectra from the dissolved sample, and for comparing said emission spectra with emission spectra produced by a known amount of a known alloy of the same metal as the sample metal to determine the composition of the sample metal.

9. Apparatus of claim 8 in which the receptacle means is a ball valve structure, the ball of said structure being rotatable and having a recess for receiving the particles from the cyclone device and for dropping the particles to the cup when the ball of the valve is rotated.

10. Apparatus for analyzing the composition of aluminum particles received from a source of said particles, comprising:

means for forming a gas stream to transport said particles from the source of the particles to a cyclone device, a cyclone device for receiving the particles transported by the gas stream, valve means for interrupting the gas stream, a ball valve located beneath the cyclone device and having a recess in the ball of the valve for receiving the particles from the cyclone device when the gas stream is interrupted, at least two cups joined together for receiving particles from said ball valve and which when each is filled to maximum capacity will hold substantially the same amount of metal particles each time it is filled, and when rotated to empty one cup, the other is positioned to receive metal particles from the ball valve, said cups each having an upper bevelled edge in the particle receiving position for diverting particles not collected in the cup from the cup, means for diverting excess particles from the cup to a scrap location, a dissolution vessel located beneath said cup, a funnel and ball valve means located between the cup and dissolution vessel for receiving the amount of particles from the cup and for depositing the same in the dissolution vessel, a pipette and valve system connected to the dissolution vessel for supplying a known amount of solvent to the dissolution vessel to dissolve the metal particles and provide a dissolved sample of metal for analysis, an optical emission spectrometer connected to receive the dissolved sample from the dissolution vessel for producing emission spectra from the dissolved sample, and for comparing said emission spectra with emission spectra produced by a known amount of a known alloy of the same metal as the sample metal to determine the composition of the sample metal, means for supplying standards for calibrating the emission spectrometer, a liquid supply means for flushing the spectrometer, and a valve system that provides flushing by said liquid whenever the spectrometer is free of sample or standard materials.

* * * * *

UNITED STATES PATENT AND TRADEMARK OFFICE
CERTIFICATE OF CORRECTION

PATENT NO. : 5,110,553

DATED : May 5, 1992

INVENTOR(S) : Michael L. Ruschak et al

It is certified that error appears in the above-identified patent and that said Letters Patent is hereby corrected as shown below:

ON THE TITLE PAGE
References Cited:

U.S. Patent Documents:

Change "3,607,099" to --3,607,094--.

Change "McAninel" to --McAninch--.

Claim 6,
Col. 7, lines 33-34     Change "producing" to --providing--.

Claim 7,
Col. 7, line 39      Change "producing" to --providing--.

Signed and Sealed this

Twenty-ninth Day of June, 1993

Attest:

MICHAEL K. KIRK

Attesting Officer      Acting Commissioner of Patents and Trademarks